US00PP16772P2

(12) United States Plant Patent
Pierce

(10) Patent No.: US PP16,772 P2
(45) Date of Patent: Jul. 4, 2006

(54) ***CALIBRACHOA* PLANT NAMED 'CAL ROSTAR'**

(50) Latin Name: ***Calibrachoa* sp.**
Varietal Denomination: Cal Rostar

(75) Inventor: Robert Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 83 days.

(21) Appl. No.: 11/091,667

(22) Filed: Mar. 28, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Jondle & Associates P.C.

(57) ABSTRACT

A *Calibrachoa* cultivar particularly distinguished by flowers with a cream/white background and margins with red-purple petals and veining is disclosed.

1 Drawing Sheet

Figure 1:
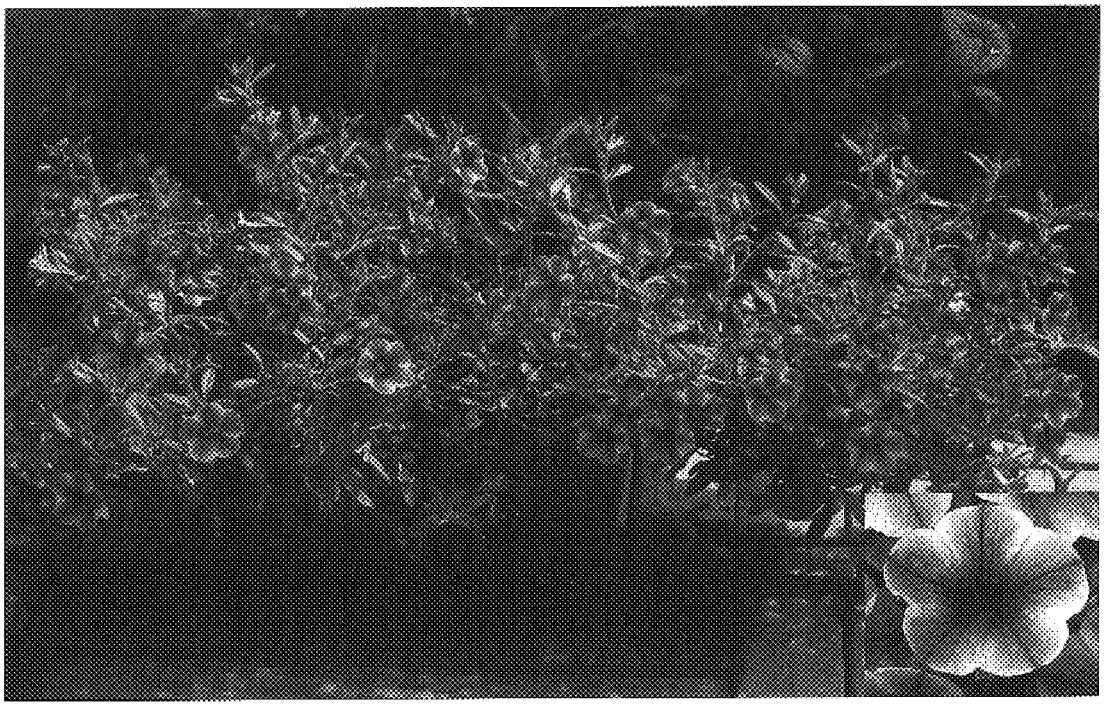

Genus and species: *Calibrachoa* sp.
Variety denomination: 'Cal Rostar'.

BACKGROUND OF THE INVENTION

The present invention comprises a new and distinct cultivar of *Calibrachoa*, botanically known as *Calibrachoa* sp., and hereinafter referred to by the cultivar name 'Cal Rostar'. The new cultivar originated from a hybridization made in the year 2001 in Gilroy, Calif. The female parent was proprietary *Calibrachoa* breeding line 360-2 (unpatented) with coral star flowers. The male parent was proprietary *Calibrachoa* breeding line 388-2 (unpatented) with rose star flowers.

The new cultivar was created in 2001 in Gilroy, Calif. and has been asexually reproduced over a two-and-a-half-year period by vegetative cuttings and tissue culture in Gilroy, Calif. and Andijk, The Netherlands. The plant has also been trialed at Gilroy, Calif., Litchfield, Mich. and Andijk, The Netherlands. 'Cal Rostar' has been found to retain its distinctive characteristics through successive asexual propagations. 'Cal Rostar' reproduces true to type through successive generations of asexual reproduction.

Description of the genus *Calibrachoa* Llave & Lex

The genus *Petunia* was originally established in 1803 by A. L. Jussieu, who described both *P. parviflora* and *P. nyctaginiflora* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida*, the Garden *Petunia*, and the inter-relationship of several species classified as *Petunia*. These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the *Petunia* genus, Wijsman and J. H. de Jong proposed transferring the 14 chromosome species to the genus *Stimoryne*. Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa*, originally established by Llave and Lexarza in 1825. *Calibrachoa parviflora* (=*C. mexicana* Llave & Lexarza) is now the type species for the genus *Calibrachoa*.

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* species bear a flower peduncle and three stems. *Petunia* species have a cochlear corolla bud, a single outermost petal which covers the other four, and radially folded and terminally contorted petals. *Calibrachoa* flower buds are flat with all five petals linearly folded with the two lower petals forming a cover around the three other petals and fused together.

DESCRIPTION OF PHOTOGRAPH

This new *Calibrachoa* plant is illustrated by the accompanying photograph which shows blooms, buds, and foliage of the plant; the colors shown are as true as can be reasonably obtained by conventional photographic procedures. The photograph is of a three-month-old plant grown in a lexan-covered greenhouse.

FIG. 1 shows overall plant habit while the inset photograph show a closer view of the mature inflorescence.

DETAILED DESCRIPTION OF THE NEW PLANT

The following detailed descriptions set forth the distinctive characteristics of 'Cal Rostar'. The data which defines these characteristics were collected from asexual reproductions carried out in Gilroy, Calif. The plant history was taken on four-month-old plants grown in one-gallon pots in a poly-covered greenhouse during the summer season. Color references are primarily to The R.H.S. Colour Chart of The Royal Horticultural Society of London (R.H.S.) (2001). Texture description data were collected by viewing plant parts with a dissecting microscope.

Classification:
- *Family*.—Solanaceae.
- *Species*.—*Calibrachoa* sp.

Growth:
- *Form*.—Semi upright and decumbent.
- *Growth and branching habit*.—Good vigorous habit, well branched, full plant.
- *Height*.—5–10 cm.
- *Width*.—55–65 cm.
- *Time to produce a finished flowering plant*.—8–10 weeks.
- *Outdoors plant performance*.—Does well in full sun; free flowering through the summer; some heat tolerance. Used as a hanging plant or in mixed containers.
- *Time to initiate and develop roots*.—18–23 days.
- *Root description*.—White, fibrous.

Stems:
- *Color*.—RHS 144A.
- *Length*.—40–55 cm.
- *Diameter*.—0.2–0.25 cm.
- *Internode length*.—1.5–1.8 cm.
- *Texture*.—Glandular hairs of various sizes.
- *Anthocyanin*.—None.
- *Peduncle*.—Color: RHS 144A. Length: 1.5–2.0 cm. Diameter: 0.1 cm. Texture: Many glandular hairs of various sizes.

Leaves:
- *Arrangement*.—Alternate; upper leaves sub-opposite.
- *Leaf color*. —Upper surface: RHS 137A. Lower surface: RHS 137D.
- *Length*.—3.4–4.0 cm.
- *Width*.—0.6–0.9 cm.
- *Shape*.—Oblong/elliptic.
- *Margin*.—Entire.
- *Apex*.—Obtuse.
- *Base*.—Acuminate.
- *Texture*.—Many glandular hairs.
- *Venation*.—Pinnate.
- *Venation color*.—RHS 144B.
- *Petiole*.—Color: RHS 144B. Length: 0.2–0.3 cm. Width: 0.1 cm. Texture: Many glandular hairs.

Flower bud:
- *Color at tight bud*.—RHS 3D.
- *Bud shape*.—Oblong.
- *Bud diameter*.—0.3–0.6 cm.
- *Bud length*.—1.3–2.0 cm.

Inflorescence:
- *Blooming habit*.—Continuous throughout the growing season. Good floriferousness.
- *Inflorescence type*.—Flowers solitary in upper leaf axis.
- *Lastingness of individual blooms*.—5–8 days.
- *Fragrance*.—None.
- *Floret type*.—Funnel form, 5 lobed petals, fused at base.
- *Flower diameter*.—2.5 cm.
- *Flower depth*.—1.7 cm.

Flowers:
- *Immature flower*.—Color, Upper surface: Main petal color shades between RHS 63A & RHS 63B; petal margins of RHS N155B. Main veins: RHS 59A. Secondary veins: RHS 61B. Diameter: 2.2–2.4 cm.
- *Mature flower color*.—Upper surface: Petal color between shadings of RHS 63B and RHS 63C; RHS 64A at the corolla opening; margins RHS N155B. Main veins: RHS 59B. Secondary veins: A little lighter than RHS 61B.
- *Mature flower color*.—Lower surface: Base color RHS N155D; margins RHS 36D. Main veins: RHS 175A. Secondary veins: RHS 176C.
- *Corolla*.—Tube color inside: RHS 11A; veins RHS 176C. Tube color outside: RHS 11D. Tube length: 1.5 cm. Tube diameter at opening: 0.7 cm. Texture: Glandular hairs at various sizes.
- *Petals*.—Shape: Spathulate. Apex: Rounded, some are Mucronulate. Based: Fused. Margin: Entire. Waviness of petals: None. Length: 1.1 cm. Width: 1.3 cm. Lobation: Moderate. Texture: Papillose.
- *Sepals*.—Number: 5. Color, Lower surface: RHS 137C. Length: 0.5–0.7 cm. Width: 0.3 cm. Shape: Linear. Apex: Acute. Margin: Entire. Texture: Many glandular hairs of various sizes.

Reproductive organs:
- *Stamens*.—5; 2 taller, 3 shorter.
- *Filament color*.—RHS 154C.
- *Pollen color*.—RHS 8A.
- *Pollen amount*.—Moderate.
- *Pistil*.—1.
- *Pistil length*.—0.9 cm.
- *Stigma color*.—RHS 143B.
- *Style color*.—RHS 143C.
- *Fruit/seed set*.—Not observed.

Disease and insect resistance: Not observed.

COMPARISON WITH KNOWN CULTIVARS

'Cal Rostar' differs from the female parent 360-2 (unpatented) by being earlier to flower, more prostate and by having more basal branching. 'Cal Rostar' differs from the male parent 388-2 (unpatented) by having larger flowers, more center flowering and darker green leaves.

'Cal Rostar' differs from the commercial variety 'Mini Famous Yellow Lilac Star' (U.S. Patent status unknown) by having a more compact plant habit, with larger, flatter flowers. In addition, the 'Cal Rostar' flower has a cream/white background and margins with red-purple petals and veining, while the 'Mini Famous Yellow Lilac Star' flower has a yellow background with only red-purple veining.

What is claimed is:

1. A new and distinct *Calibrachoa* plant as shown and described herein.

* * * * *